United States Patent [19]

Obendorf et al.

[11] 4,025,550

[45] May 24, 1977

[54] DERIVATIVES OF TRIIODO-AMINOBENZENECARBOXYLIC ACIDS AND THE PREPARATION THEREOF

[75] Inventors: Werner Obendorf; Irmgard Lindner; Ernst Schwarzinger; Josef Krieger, all of Linz (Danube), Austria

[73] Assignee: Chemie Linz Aktiengesellschaft, Linz (Danube), Austria

[22] Filed: Mar. 28, 1975

[21] Appl. No.: 562,933

Related U.S. Application Data

[62] Division of Ser. No. 381,337, July 20, 1973, Pat. No. 3,890,318.

[30] Foreign Application Priority Data

July 21, 1972 Germany .......................... 2235935

[52] U.S. Cl. ..................... 260/518 A; 260/471 A; 260/501.17; 260/501.13; 536/18
[51] Int. Cl.² .......................................... C07C 63/04
[58] Field of Search ....... 260/518 A, 471 A, 211 R; 424/5

[56] References Cited

UNITED STATES PATENTS

| | | | |
|---|---|---|---|
| 3,661,975 | 5/1972 | Korver ........................... | 260/518 A |
| 3,812,151 | 5/1974 | Pfeiffer et al. ................. | 260/518 A |
| 3,853,866 | 12/1974 | Obendorf et al. ............. | 260/518 A |
| 3,883,578 | 5/1975 | Gries ............................. | 260/518 A |

*Primary Examiner*—James O. Thomas, Jr.
*Assistant Examiner*—James H. Reamer
*Attorney, Agent, or Firm*—Wenderoth, Lind & Ponack

[57] ABSTRACT

Derivatives of triiodo-aminobenzene carboxylic acids having the general formula:

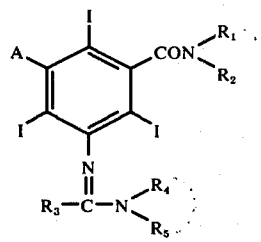

a process for their preparation and X-ray contrast agents containing them.

5 Claims, No Drawings

DERIVATIVES OF TRIIODO-AMINOBENZENECARBOXYLIC ACIDS AND THE PREPARATION THEREOF

This is a division of application Ser. No. 381,337, filed July 20, 1973 now U.S. Pat. No. 3,890,318.

The present invention relates to derivatives of triiodoaminobenzene carboxylic acids and to a process for the preparation thereof. The invention also relates to X-ray contrast agents containing these compounds.

More particularly, the present invention provides derivatives of triiodo-aminobenzene carboxylic acids having the general formula:

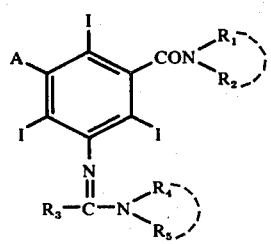

in which A is a hydrogen atom, a carboxyl group or the

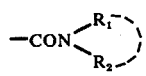

group, $R_1$ is a hydrogen atom, an alkyl or alkenyl group containing up to four carbon atoms, an alkoxyalkyl group containing up to six carbon atoms, or a benzyl or phenyl group, $R_2$ is a lower alkyl or alkenyl group or the $-R_6-COOH$ group or $R_1$ and $R_2$ together with the nitrogen atom form a morpholino, piperidino or pyrrolidino group, $R_3$ is a hydrogen atom, an alkyl group containing up to four carbon atoms or an alkylene-carboxylic acid group containing up to four carbon atoms, $R_4$ is a hydrogen atom or a lower alkyl group, $R_5$ is an alkyl or alkenyl group containing up to four carbon atoms, an alkoxyalkyl group containing up to six carbon atoms, a benzyl group or a phenyl group or $R_4$ and $R_5$ together with the nitrogen atom form a pyrrolidino, piperidino or morpholino group, and $R_6$ is a straight-chain or branched alkylene group containing up to five carbon atoms, and when $R_2$ is a lower alkyl or alkenyl group, either A is a carboxyl group or $R_3$ is an alkylenecarboxylic acid group, or a lower alkyl ester thereof, or a pharmaceutically acceptable salt thereof with an inorganic or organic base or with an inorganic or organic acid, because of the amphoteric character of the compounds of the formula (I).

Particularly preferred compounds of the formula (I) are those in which $R_1$ is as defined above, $R_2$ is a methyl, ethyl or allyl group, $R_3$ is an ethylenecarboxylic acid group or α-methylethylenecarboxylic acid group and each of $R_4$ and $R_5$ is a methyl or ethyl group, with A being a hydrogen atom, or those compounds in which $R_2$ is the group

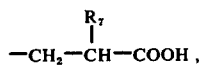

in which $R_7$ is a hydrogen atom, or a methyl or ethyl group, $R_3$ is a hydrogen atom, or a methyl or ethyl group, and each of $R_4$ and $R_5$ is a methyl group or, conjointly with the nitrogen atom, form a morpholino group, A is a hydrogen atom and $R_1$ is as defined in formula (I), and the lower alkyl ester thereof and the pharmaceutically acceptable salt thereof.

The compounds according to the invention are X-ray contrast agents for rendering the gall bladder visible, which are distinguished by low toxicity, good resorption and rapid elimination from the body. They are mostly cholecystography agents which are eliminated to the extent of 80% or more within five hours after administration, so that the administration and investigation can be carried out in one day. Some compounds of this group also may be employed as intravenous contrast agents; thus, for example, the compound N-[3-(1'-3''-oxapenta-methyleneamino-ethylideneamino)-2,4,6-triiodobenzoyl]-β-amino-propionic acid, having an intravenous toxicity of 1.75 g/kg, may be employed both as an oral and as an intravenous bile contrast agent, which is a combination which is very rare. The compound shows, after intravenous administration, a maximum concentration in the bile of about 900 mg%, and, after oral administration, a maximum concentration of about 760 mg%, and, in the latter case, is eliminated to the extent of 79% after five hours. The lower degree of bonding to protein, which in most cases is less than 50%, also indicates the ease of elimination. In addition to this and other compounds which possess an oxapenta-methylene grouping and have advantageous properties, such as, for example, N-[3-(1',3''-oxapentamethyleneamino-ethylideneamino)-2',4',6'-triiodobenzoyl]-β-amino-α-methylpropionic acid with an intravenous toxicity of 1.27 g/kg and 89% elimination after five hours, the compounds N-[3-(1'-dimethylamino-ethylideneamino)-2,4,6-triiodobenzoyl]-β-amino-α-methyl-propionic acid, N-[3-(1'-dimethylamino-ethylideneamino)-2,4,6-triiodobenzoyl]-N-(δ'-methoxy-propyl)-β-aminopropionic acid and N-[3-(1'-ethyl-amino-ethylideneamino)-2,4,6-triiodobenzoyl]-N-methyl-β-amino-propionic acid also may be mentioned as examples, because of their good properties.

The present invention also provides a process for the preparation of a compound of formula (I) herein, which comprises reacting a derivative of a triiodoaminobenzene carboxylic acid having the general formula:

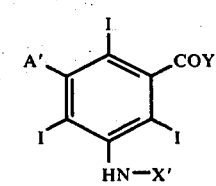

with a compound having the general formula:

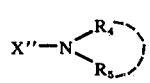

wherein, in the formula (II), Y is a halogen atom or the group

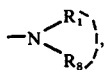

A' is a hydrogen atom, a carboxyl group, a carboxyl group esterified by an aliphatic alcohol, an acid chloride group or the

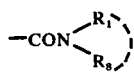

group, in which $R_8$ is a lower alkyl or alkenyl group or the group $R_6.COOH$ or $R_6.COOalkyl$, or $R_8$ together with $R_1$ and the nitrogen atom forms a morpholino, piperidino or pyrrolidino group, and in the formulae (II) and (III) one of X' and X'' is a hydrogen atom, and the other is the $-COR_9$ group, wherein $R_9$ is a hydrogen atom, an alkyl group containing up to four carbon atoms, an alkylenecarboxylic acid group containing up to four carbon atoms or an alkylenecarboxylic acid alkyl ester group, in which the acid component contains up to four carbon atoms, and in the formulae (II) and (III) $R_1$, $R_4$, $R_5$ and $R_6$ are as defined in formula (I) and, when $R_8$ is a lower alkyl or alkenyl group, either A' is a carboxyl group or an alkyl ester thereof or $R_9$ is an alkylenecarboxylic acid group or alkylenecarboxylic acid alkyl ester group, and with at least 1 mol of a halide of pentavalent phosphorus, preferably in an inert organic solvent, and in the resulting compounds or their hydrochlorides, subsequently reacting the acid chloride group present in the aromatic nucleus with an amine having the formula:

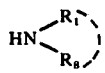

(IV)

in which $R_1$ and $R_8$ are as defined above and, if desired, saponifying ester groups which are present, and, if desired, converting acid or basic groups which are present into salts or liberating acids or bases from such salts.

The compounds obtained by the above process may be isolated as the free amphoteric compound, as an ester thereof or as a salt either with a base or with an acid.

The process may be carried out in two important variants. According to one variant, a compound of the formula (II), in which X' is a hydrogen atom, that is to say 3-amino-2,4,6-triiodobenzoyl chloride, or a 3-amino-2,4,6-triiodobenzoic acid amide derived therefrom, is reacted with an acid amide of the formula (III) in which X'' is the group $R_9CO-$. The reaction temperature in this case may be 20° to 100° C, and an elevated temperature accelerates the reaction. The reaction is appropriately carried out in a suitable solvent such as toluene, chloroform, ethyl, ethyl acetate or dioxane. The amide of formula (III), which must then be present in excess, may also serve as the solvent. As the phosphorus halide, $POCl_3$ is preferably employed in this case, appropriately in an amount of at least 1 mol of $POCl_3$ per mol of compound of the formula (II).

It is, however, also possible for the acid amide group to be bonded to the benzene nucleus and the reaction to be carried out with an amine of the formula (III) (X'' = H). In this variant of the process it is advisable to carry out the reaction at room temperature and in the presence of at least 1 mol of phosphorus pentachloride per mol of compound of the formula (II), chlorinated hydrocarbons having proved particularly suitable as solvents.

The product of the reaction of both variants of the process may be isolated either as the hydrochloride or as the base, the latter being liberated by rendering the reaction solution alkaline. If Y is in the formula (II) is a halogen atom, the acid chloride group subsequently must be converted into the amide group, which is easily possible by reaction with the appropriate amine. If A' in the formula I is also an acid chloride group, this is also simultaneously converted into the amide group, and this fact must be taken into account in deciding the amount of the amine of the formula (IV).

Ester groups present in the molecule may be saponified subsequently in the usual manner. The compound obtained may be isolated from the saponification solution, which, in most cases, is alkaline, as a salt of the acid or as the free acid. It may also be isolated as a salt with an acid. The isolation of the free carboxylic acids of the formula (I) takes place particularly favourably if an aqueous solution of a salt of these carboxylic acids of the formula (I), or a salt of these compounds with acids, is adjusted by means of an acid or base to the intrinsic pH of the free amidinecarboxylic acid. The latter then precipitate in most cases as an amorphous product and, if necessary, may be purified by recrystallization. The melting points of the amorphous products are not characteristic.

Suitable salts of the compounds according to the invention are sodium, lithium and ammonium salts, salts of the alkaline earth metals and salts of non-toxic organic bases such as glucosamine, methylglucosamine, ethanolamine, diethanolamine, glucamine and methylglucamine.

Examples of salts of the amidines or of the esters which are used are the hydrochlorides, sulphates, acetates, fumarates, succinates and tartrates.

Because of the structure, isomerism may occur. The individual isomers may be so stable that they may be isolated in the pure form. These isomers are also within the scope of the present invention.

The compounds of the formulae (II), (III) and (IV) are known and are accessible according to methods described in the literature. In this context, attention is drawn to Austrian Patent Specifications Nos. 209,895 ad 224,264 and to German Patent Specifications Nos. 1,117,135 and 1,082,368.

The compounds according to the invention, used as X-ray contrast agents, may be administered orally in the form of tablets, dragees, powders or granules, packaged in capsules or as effervescent powders. Either free acids or salts with bases or acids may be employed for these preparations. For intravenous administration, aqueous solutions of the salts with inorganic or organic bases are preferably employed.

The following Examples illustrate the preparation of compounds according to the invention and compositions containing such compounds.

EXAMPLE 1

133.3 g. of 3-amino-2,4,6-triiodobenzoyl chloride are dissolved in toluene, 37.5 ml. of dimethylformamide and 31.3 ml. of POCl₃ are added and the solution is subsequently boiled for 1 hour under reflux. The hydrochloride of 3-dimethylaminomethyleneimino-2,4,6-triiodobenzoyl chloride which is thereby produced is filtered off after cooling and is washed with water. Then this product is covered with ether, water is added, and 250 ml. of a 4N sodium hydroxide solution are added dropwise whilst cooling with ice and stirring well. The ether layer is separated off, washed with ice water, dried over sodium chloride and evaporated. The oily evaporation residue is dissolved in hot cyclohexane and the solution is treated with active charcoal and clarified by filtration. On slow cooling, 123.37 g. of yellow 3-dimethylaminomethyleneamino-2,4,6-triiodobenzoyl chloride crystallise therefrom, melting point:- 100° to 105° C.

58.8 g. of the acid chloride obtained are dissolved in chloroform and a solution of 30.0 g. of N-allyl-β-aminopropionic acid methyl ester in chloroform is added. The reaction mixture begins to boil; to complete the reaction, it is boiled for a further 2 hours under reflux and the solution is then washed with water, 5% strength tartaric acid and potassium carbonate solution, dried over calcium chloride and evaporated. The residue is dissolved in hot methanol and 30.0 g. of N-(3-dimethylaminomethyleneamino-2,4,6-triiodobenzoyl)-N-allyl-β-aminopropionic acid methyl ester of melting point:- 86° to 98° C crystallise out; on concentrating the mother liquor to one-third, a further 22.0 g. of melting point:- 85° to 100° C crystallise out.

25 g. of the ester are saponified in excess aqueous sodium hydroxide at 80° C and the resulting solution is clarified by filtration and when cold is adjusted to pH 6 with hydrochloric acid. The amorphous precipitate is triturated under ice water, filtered off and dried in a desiccator. The yield is 22.0 g. of amorphous N-(3-dimethylaminomethyleneamino-2,4,6-triiodobenzoyl)-N-allyl-β-aminopropionic acid. Melting point:- 94° to 106° C.

EXAMPLE 2

6.76 g. of N-(3-amino-2,4,6-triiodobenzoyl)-N-phenyl-β-aminopropionic acid methyl ester are dissolved in absolute toluene and after addition of 1.5 ml. of dimethylforamide and 1.25 ml. of POCl₃ the mixture is boiled for 1 hour. The oil which hereupon separates out is separated off after cooling, dissolved in methanol and reprecipitated with ether. On trituration with ether, crystallisation occurs. Yield, 6.2 g. of brownish hydrochloride of N-(3-dimethyl-aminomethylene-amino-2,4,6-triiodobenzoyl)-N-phenyl-β-aminopropionic acid methyl ester, melting point:- 130° to 135° C. Treatment thereof with excess NaHCO₃ yields the ester base of melting point:- 70° to 77° C, which may be saponified with aqueous caustic alkali in the same manner as in Example 1. The melting point of the amorphous N-(3-dimethylaminomethyleneamino-2,4,6-triiodobenzoyl)-N-phenyl-β-aminopropionic acid is 92° to 116° C.

EXAMPLE 3

18.0 g. of the acid chloride manufactured according to Example 1 are dissolved in chloroform and 9.5 g. of ε-aminocaproic acid methyl ester, dissolved in chloroform, are added. The reacton mixture comes to the boil. It is boiled for a further 90 minutes and the chloroform solution is then washed with water, aqueous tartaric acid solution and potassium carbonate solution, dried with calcium chloride and evaporated. The evaporation residue is dissolved in hot methanol and clarified by filtration. 14.0 g. of N-(3-dimethylaminomethyleneamino-2,4,6-triiodobenzoyl)-ε-aminocaproic acid methyl ester, melting point:- 139° to 142° C, crystallise from the solution, and on concentrating the mother liquor a further 6.2 g. of the same product crystallise, melting point:- 128° to 140° C. For saponification, 18.0 g. of this ester are suspended in 2N sodium hydroxide and boiled until completely dissolved. After filtration, the pH is adjusted to 5 with dilute hydrochloric acid, whereupon the acid is obtained as an oil and solidifies on cooling with ice water. After filtration, and drying in a desiccator, 12.0 g. of amorphous N-(3-dimethylaminomethyleneamino-2,4,6-triiodobenzoyl)-δ-aminocaproic acid, melting point:- 90° to 100° C, are obtained.

EXAMPLE 4

213.2 g. of 3-amino-2,4,6-triiodobenzoyl chloride are dissolved in chloroform, 174 g. of dimethylacetamide are added and 153 g. of POCl₃ are added dropwise over the course of 20 minutes, during which the mixture comes to the boil. It is boiled for a further 8 hours and after cooling the crystals obtained are filtered off. The crystals are suspended in ether and shaken with ice-cold, dilute sodium hydroxide solution until all the material has dissolved. On concentrating the ether phase after drying with sodium sulphate, 127.0 g. of 3-(1'-dimethylamino-ethylideneamino)-2,4,6-triiodobenzoyl chloride of melting point:- 127° to 130° C. crystallise out.

39.13 g. of this acid chloride are dissolved in chloroform, 25.0 g. of N-(3-methoxypropyl)-β-aminopropionic acid methyl ester are added dropwise, whereupon the mixture becomes warm, and the reaction mixture is boiled for 40 minutes. The resulting solution is washed with water and potassium bicarbonate solution, dried over sodium sulphate and evaporated. The evaporation residue is boiled with 0.7N methanolic sodium hydroxide until completely saponified and thereafter the solvent is distilled off. The residue is dissolved in water and the acid is precipitated with acetic acid, filtered off and dried in vacuo. 16.8 g. of amorphous N-[3-(1'-dimethylamino-ethylideneamino)-2,4,6-triiodobenzoyl]-N-(δ'-methoxypropyl)-β-aminopropionic acid, melting point:- 90° to 110° C, are obtained.

EXAMPLE 5

213.2 g. of 3-amino-2,4,6-triiodobenzoyl chloride are dissolved in chloroform, 135 g. of acetanilide are added, followed by 153 g. of POCl₃ added over the course of 15 minutes, and the solution is boiled for 8 hours. After cooling, the crystals obtained are filtered off. The crystals are suspended in chloroform and cold dilute sodium hydroxide is added whilst stirring, which produces a solution. The chloroform phase is separated off, washed with water, dried over sodium sulphate and concentrated, whereupon 220 g. of 3-(1'-phenylamino-ethylideneamino)-2,4,6-triiodobenzoyl chloride crystallise, melting point:- 172° to 178° C.

52.0 g. of the acid chloride are dissolved in chloroform and 26.0 g. of N-methyl-β-amino-α-methylpropionic acid methyl ester are added. After the exothermic reaction has subsided, the solution is boiled for a further 30 minutes and is then washed with water and potassium bicarbonate solution, dried over sodium sulphate and evaporated. The evaporation residue is boiled in approximately 1N methanolic sodium hydroxide until completely saponified. After distilling off the solvent, the residue is taken up in water and acetic acid is added until the acid has been precipitated completely. The precipitate is filtered off and dried. The yield is 56.0 g. of amorphous N-[3-(1'-phenylaminoethylideneamino)-2,4,6-triiodobenzoyl]-N-methyl-β-amino-α-methylpropionic acid, melting point:- 142° to 166° C.

EXAMPLE 6

53.3 g. of 3-amino-2,4,6-triiodobenzoyl chloride are dissolved in chloroform, 39 g. of N-acetylmorpholine and 45 g. of $POCl_3$ are added and the mixture is boiled for 6 hours. After cooling, the crystals obtained are filtered off, washed with chloroform and dried. 61.0 g. of hydrochloride of 3-(1'-3''-oxapentamethyleneamino-ethylideneamino)-2,4,6-triiodobenzoyl chloride are obtained, melting point from 240° C. onwards, with decomposition.

27.2 g. of the resulting compound are suspended in chloroform and the amidine base is liberated by adding triethylamine and is reacted with 12.0 g. of β-aminopropionic acid ethyl ester. After the reaction has subsided, the reaction mixture is additionally boiled for 15 minutes and the resulting chloroform solution is washed with water, dried over sodium sulphate and evaporated. The evaporation residue is boiled with approximately 0.6N methanolic aqueous sodium hydroxide under reflux until saponification has occurred. After distilling off the solvent, the residue is taken up in water and the acid produced is precipitated with glacial acetic acid, filtered off and dried. 24.8 g. of amorphous N-[3-(1'-3''-oxapentamethyleneamino-ethylideneamino)-2,4,6-triiodobenzoyl]-β-aminopropionic acid are obtained, melting point:- 133° to 145° C.

EXAMPLE 7

27.2 g. of acid chloride hydrochloride, manufactured according to Example 6, are suspended in chloroform, triethylamine to liberate the aminide, and 11.7 g. of β-amino-α-methyl propionic acid methyl ester, are added, and the solution is boiled for 20 minutes. The working up, saponification and precipitation of the end product take place in the same manner as in Example 6. 25.5 g. of amorphous N-[3-(1'-3''-oxapentamethyleneamino-ethylideneamino)-2,4,6-triiodobenzoyl]-β-amino-α-methylpropionic acid are thus obtained, melting point:- 131° to 148° C. The acid crystallises from ethyl acetate and than has a melting point:- 291° to 294° C.

If the chloroform solution from the reaction of acid chloride with aminocarboxylic acid ester is washed with caustic alkali solution and evaporated and the residue is taken up in methanol, the methyl ester of N-[3-(1'-3''-oxapentamethyleneamino-ethylideneamino)-2,4,6-triiodobenzoyl]-β-amino-α-methylpropionic acid crystallises, melting point:- 166° to 172° C.

35.0 g. of N-[3-(1'-3''-oxapentamethyleneamino-ethylideneamino)-2,4,6-triiodobenzoyl]-β-amino-α-methylpropionic acid are dissolved in 250 ml. of hot water after addition of 25 ml. of 4N hydrochloric acid. On cooling, the salt crystallises out. After filtration and drying, 32.0 g. of hydrochloride of N-[3-(1'-3''-oxapentamethylene-amino-ethylideneamino)-2,4,6-triiodobenzoyl]-β-amino-α-methylpropionic acid are obtained, melting point:- slow melting at 235° C, decomposition from 255° C onwards.

EXAMPLE 8

32.8 g. of N-(3-acetylamino-2,4,6-triiodobenzoyl)-β-amino-α-methylpropionic acid methyl ester are dissolved in methylene chloride and 13.35 g. of $PCl_5$ are added. This suspension is stirred for 17 hours, in the course of which the reaction products gradually dissolve, and morpholine is then added, whilst cooling with ice, until an alkaline reaction persists. After standing for approximately 45 hours at room temperature, the crystals which have precipitated are filtered off and the filtrate is washed with water, dried and evaporated. The evaporation residue, 43.5 g. of a pale oil, are saponified with aqueous-methanolic sodium hydroxide as in preceding experiments and N-[3-(1'-3''-oxapentamethyleneaminoethylideneamino)-2,4,6-triiodobenzoyl]-β-amino-α-methylpropionic acid is precipitated from the aqueous solution with hydrochloric acid. Yield 15.8 g.; the product is the same as the compound obtained according to Example 7.

EXAMPLE 9

24.0 g. of N-(3-amino-2,4,6-triiodobenzoyl)-aminoacetic acid ethyl ester are dissolved in chloroform, 6.2 g. of N-acetylmorpholine and 7.4 g. of $POCl_3$ are added and the solution is boiled for 5 hours. After standing overnight, the mixture is filtered, the crystals, whilst still moist, are dissolved in methanol and boiled up, and aqueous sodium hydroxide solution is added until saponification is complete. The solvent is then distilled off, the residue is taken up in water and the solution is clarified by filtration and adjusted to pH 5 with dilute hydrochloric acid. The amorphous acid which hereupon precipitates is caused to crystallise by gentle warming and is filtered off cold and dried at 110° C. The yield is 12.5 g. of N-[3-(1'-3''-oxapentamethyleneamino-ethylideneamino)-2,4,6-triiodobenzoyl]-aminoacetic acid, melting point:- 265° to 270° C., with decomposition.

EXAMPLE 10

21.32 g. of 3-amino-2,4,6-triiodobenzoyl chloride are dissolved in chloroform, 17.2 g. of N-propionylmorpholine and 18.0 g. of $POCl_3$ are added, and the mixture is boiled for 5 hours. After cooling, the crystals which have precipitated are filtered off, washed with chloroform and dried. 23.4 g. of 3-(1'-3''-oxapentamethylene-amino-propylideneamino)-2,4,6-triiodobenzoyl chloride hydrochloride are obtained. The amidine base is prepared in an analogous manner to that of Example 4 and has a melting point:- 147° to 151° C.

27.80 g. of the acid chloride hydrochloride are suspended in chloroform, triethylamine is added to liberate the amidine base, thereafter 12.0 g. of β-amino-α-methylpropionic acid methyl ester are added, and the reaction mixture is boiled for 30 minutes. After cooling, the reaction solution is washed with water and dilute hydrochloric acid, dried over sodium sulphate and evaporated. The evaporation residue is heated with aqueous methanolic sodium hydroxide until saponification is complete. After distilling off the solvent, the residue is taken up in water, the solution is clarified by filtration, and the acid is precipitated with glacial acetic acid and filtered off. After treatment with water, and vacuum drying, 25.6 g. of amorphous N-[3-(1'-3''-oxapentamethyleneamino-propylideneamino)-2,4,6- triiodobenzoyl]-β-amino-α-methylpropionic acid are obtained, melting point:- 130° to 145° C.

EXAMPLE 11

53.3 g. of 3-amino-2,4,6-triiodobenzoyl chloride are dissolved in chloroform, 48 g. of succinic acid dimethylamide monomethyl ester and 45 g. of $POCl_3$ are added and the mixture is boiled for 7 hours. The solution is then poured onto ice and the chloroform phase is separated off, washed with dilute sodium hydroxide solution and water, dried and evaporated. The evaporation residue is taken up in ether, the insoluble portion (10.4 g.) is filtered off and the solution is evaporated to dryness. 45.2 g. of 3-(3'-chloroformyl-2',4',6'-triiodoanilino)-3-dimethylaminopropylidene-(3)-carboxylic acid methyl ester are obtained in the form of an oil which can be directly reacted further.

The crude acid chloride is dissolved in chloroform, excess methylamine is passed in and the reaction mixture is boiled for 10 minutes. Thereafter it is washed with water, dried over sodium sulphate and evaporated. The evaporation residue is saponified in aqueous methanolic sodium hydroxide solution at the boil, the methanol is distilled off, the residue is diluted with water, and after clarification by filtration the acid is liberated by means of glacial acetic acid. On warming, the initially amorphous precipitate becomes crystalline. The crystals are filtered off and boiled with methanol. Yield 16.9 g. of 3-(3'-N-methylcarbamyl-2',4',6'-triiodoanilino)-3-dimethylamino-propylidene-(3)-carboxylic acid of melting point:- 264° to 268° C.

EXAMPLE 12

53.3 g. of 3-amino-2,4,6-triiodobenzoyl chloride are dissolved in chloroform, 37.8 g. of succinic acid morpholino monomethyl ester and 30.6 g. of $POCl_3$ are added and the solution is boiled for 6 hours. After standing overnight, the crystals produced are filtered off, washed with chloroform and dried. The yield is 24.5 g. of hydrochloride of 3-(3'-chloroformyl-2',4',6'-triiodoanilino)-3-(3''-oxapentamethyleneamino)-propylidene-(3)-carboxylic acid methyl ester. The amidine base is prepared as in Example 4; it has a melting point of 132° to 134° C.

14.9 g. of the acid chloride hydrochloride are suspended in chloroform, excess methylamine is passed in and the solution is boiled for 10 minutes. After cooling, it is washed with water and dilute acetic acid and the chloroform phase is dried and evaporated. The evaporation residue is boiled with aqueous methanolic sodium hydroxide until completely saponified, the solvent is removed by evaporation and the residue is taken up in water. The acid is liberated by means of glacial acetic acid at the boil. It precipitates as crystals and is filtered off and dried.

Yield, 11.0 g. of 3-(3'-N-methylcarbamyl-2',4',6'-triiodoanilino)-3-(3''-oxapentamethyleneamino)-propylidene-(3)-carboxylic acid of melting point:- 265° to 270° C.

EXAMPLE 13

22.8 g. of 3-amino-5-N-methylcarbamyl-2,4,6-triiodobenzoic acid are suspended in dioxane, 25 ml. of dimethylformamide and 25 ml. of $POCl_3$ are added, and the mixture is boiled for 90 minutes. The reaction mixture is then evaporated to dryness in vacuo and the residue is carefully treated with 200 ml. of water. The crystals produced are filtered off and dissolved in water by addition of sodium hydroxide, the solution is clarified by filtration and the product is again precipitated, with dilute hydrochloric acid. 23.5 g. of 3-dimethylaminomethyleneamino-5-N-methylcarbamyl-2,4,6-triiodobenzoic acid hydrochloride are obtained, melting point:- from 300° C onwards, with decomposition.

EXAMPLE 14

53.1 g. of 3-amino-5-N-methylcarbamyl-2,4,6-triiodobenzoyl chloride are suspended in chloroform, 52.2 g. of dimethylacetamide and 121.8 g. of $POCl_3$ are added and the solution is boiled for 4.5 hours. After cooling, the product obtained is filtered off, suspended in chloroform and dissolved by adding triethylamine. The chloroform solution is separated off, washed with water, dried over sodium chloride and evaporated. The evaporation residue is crystallised from ether and yields 18.3 g. of 3-(1'-dimethylamino-ethylideneamino)-5N-methylcarbamyl-2,4,6-triiodobenzoyl chloride, melting point:- 235° C., with decomposition.

17.1 g. of this acid chloride are dissolved in chloroform, 11.7 g. of β-amino-α-methylpropionic acid methyl ester are added and the mixture is boiled for 1 hour. The reaction solution is washed with water, dried and evaporated. The evaporation residue is saponified by boiling with excess aqueous methanolic sodium hydroxide. After distilling off the solvent, the residue is dissolved in water and the solution is clarified by filtration and acidified with 4N hydrochloric acid. 6.3 g. of hydrochloride of N-[3-(1'-dimethylamino-ethylideneamino)-5-N-methylcarbamyl-2,4,6-triiodobenzoyl]-β-amino-α-methylpropionic acid gradually crystallise from the solution, melting point:- 266° to 273° C.

EXAMPLE 15

6.14 g. of N-(3-amino-2,4,6-triiodobenzoyl)-N-ethyl-β-aminopropionic acid are dissolved in chloroform by adding 1.5 g. of dimethylformamide and 3.0 g. of $POCl_3$ and warming. On boiling (90 minutes) an oily reaction product separates out, which, after cooling and decanting off the solvent, is dissolved in dilute aqueous sodium hydroxide. After clarifying the solution by filtration and acidifying to pH 5 with dilute hydrochloric acid, 3.7 g. of amorphous N-(3-dimethylaminomethyleneamino-2,4,6-triiodobenzoyl)-N-ethyl-β-aminopropionic acid precipitate, melting point:- 105° to 125° C.

The following compounds are prepared in an analogous manner to those of the preceding Examples:

N-(3-Dimethylamino-methyleneamino-2,4,6-triiodobenzoyl)-aminoacetic acid, melting point:- 256° to 259° C.

N-(3-Dimethylamino-methyleneamino-2,4,6-triiodobenzoyl)-N-methylaminoacetic acid, melting point:- 135° to 140° C.

N-(3-Dimethylamino-methyleneamino-2,4,6-triiodobenzoyl)-β-aminopropionic acid, melting point:- 208° to 214° C.

N-(3-Dimethylamino-methyleneamino-2,4,6-triiodobenzoyl)-N-methyl-β-aminopropionic acid, melting point:- 138° to 150° C.

N-(3-Dimethylamino-methyleneamino-2,4,6-triiodobenzoyl)-N-isopropyl-β-aminopropionic acid, melting point:- 125° to 135° C.

N-(3-Dimethylamino-methyleneamino-2,4,6-triiodobenzoyl)-N-(δ'-methoxypropyl)-β-aminopropionic acid, melting point:- 158° to 164° C.

N-(3-Dimethylamino-methyleneamino-2,4,6-triiodobenzoyl)-β-amino-α-methylpropionic acid, melting point:- 110° to 125° C.

N-[3-(3'-Oxapentamethyleneaminomethyleneamino)-2,4,6-triiodobenzoyl]-β-amino-α-methylpropionic acid, melting point:- 123° to 140° C.

N-[3-(1'-Ethylamino-ethylideneamino)-2,4,6-triiodobenzoyl]-N-methyl-β-aminopropionic acid, melting poit:- 133° to 149° C.

N-[3-(1'-Ethylamino-ethylideneamino)-2,4,6-triiodobenzoyl]-N-allyl-β-aminopropionic acid, melting point:- 122° to 139° C.

N-[3-(1'-Ethylamino-ethylideneamino)-2,4,6-triiodobenzoyl]-β-amino-α-methylpropionic acid, melting point: 148° to 157° C.

N-[3-(1'-Dimethylamino-ethylideneamino)-2,4,6-triiodobenzoyl]-N-allyl-β-aminopropionic acid, melting point:- 199° to 200° C.

N-[3-(1'-Dimethylamino-ethylideneamino)-2,4,6-triiodobenzoyl]-β-amino-α-methylpropionic acid, melting point:- 159° to 166° C.

N-[3-(1'-Dimethylamino-ethylideneamino)-2,4,6-triiodobenzoyl]-N-methyl-β-amino-α-methylpropionic acid, melting point:- 181° to 187° C.

N-[3-(1'-δ'-Methoxypropylamino-ethylideneamino)-2,4,6-triiodobenzoyl]-β-amino-α-methylpropionic acid, melting point:- 120° to 135° C.

N-[3-(1'-Phenylamino-ethylideneamino)-2,4,6-triiodobenzoyl]-N-allyl-β-aminopropionic acid, melting point:- 135° to 146° C.

N-[3-(1'-Phenylamino-ethylideneamino)-2,4,6-triiodobenzoyl]-N-(3''-methoxypropyl)-β-aminopropionic acid, melting point:- 120° to 131° C.

N-[3-(1'-Phenylamino-ethylideneamino)-2,4,6-triiodobenzoyl]-β-amino-α-methylpropionic acid, melting point:- 153° to 180° C.

N-[3-(1'-Pentamethyleneamino-ethylideneamino)-2,4,6-triiodobenzoyl]-N-allyl-β-aminopropionic acid, melting point:- 148° to 158° C.

N-[3-(1'-Pentamethyleneamino-ethylideneamino)-2,4,6-triiodobenzoyl]-N-(δ'-methoxypropyl)-β-aminopropionic acid, melting point:- 87° to 120° C.

N-[3-(1'-3''-Oxapentamethyleneamino-ethylideneamino)-2,4,6-triiodobenzoyl]-N-methyl-β-aminopropionic acid, melting point:- 154° to 158° C.

N-[3-(1'-3''-Oxapentamethyleneamino-ethylideneamino)-2,4,6-triiodobenzoyl]-N-ethyl-β-aminopropionic acid, melting point:- 130° to 138° C.

N-[3-(1'-3''-Oxapentamethyleneamino-ethylideneamino)-2,4,6-triiodobenzoyl]-N-allyl-β-aminopropionic acid, melting point:- 120° to 128° C.

N-[3-(1'-3''-Oxapentamethyleneamino-ethylideneamino)-2,4,6-triiodobenzoyl]-N-isopropyl-β-aminopropionic acid, melting point:- 140° to 152° C.

N-[3-(1'-3''-Oxapentamethyleneamino-ethylideneamino)-2,4,6-triiodobenzoyl]-N-(δ'-methoxypropyl)-β-aminopropionic acid, melting point:- 109° to 115° C.

N-[3-(1'-3''-Oxapentamethyleneamino-ethylideneamino)-2,4,6-triiodobenzoyl]-N-benzyl-β-amino-α-methylpropionic acid, melting point:- 191° to 196° C.

N-[3-(1'-3''-Oxapentamethyleneamino-ethylideneamino)-2,4,6-triiodobenzoyl]-N-propyl-β-aminobutyric acid, melting point:- 125° to 155° C.

N-[3-(1'-3''-Oxapentamethyleneamino-ethylideneamino)-2,4,6-triiodobenzoyl]-β-amino-α-ethylpropionic acid, melting point:- 125° to 130° C.

N-[3-(1'-Diethylamino-propylideneamino)-2,4,6-triiodobenzoyl]-N-methyl-β-aminopropionic acid, melting point:- 80° to 115° C.

N-[3-(1'-Diethylamino-propylideneamino)-2,4,6-triiodobenzoyl]-N-(δ'-methoxypropyl)-β-aminopropionic acid (sticky product).

N-[3-(1'-Diethylamino-propylideneamino)-2,4,6-triiodobenzoyl]-N-allyl-β-aminopropionic acid, melting point:- 93° to 105° C.

N-[3-(1'-Diethylamino-propylideneamino)-2,4,6-triiodobenzoyl]-β-amino-α-methylpropionic acid, melting point:- 113° to 123° C.

N-[3-(1'-Diethylamino-propylideneamino)-2,4,6-triiodobenzoyl]-N-methyl-β-amino-α-methylpropionic acid, melting point:- 105° to 115° C.

N-[3-(1'-3''-Oxapentamethyleneamino-propylideneamino)-2,4,6-triiodobenzoyl]-N-methyl-β-aminopropionic acid, melting point:- 114° to 125° C.

N-[3-(1'-3''-Oxapentamethyleneamino-propylideneamino)-2,4,6-triiodobenzoyl]-N-ethyl-β-aminopropionic acid, melting point:- 110° to 125° C.

N-[3-(1'-3''-Oxapentamethyleneamino-propylideneamino)-2,4,6-triiodobenzoyl]-N-allyl-β-aminopropionic acid, melting point:- 110° to 125° C.

N-[3-(1'-3''-Oxapentamethyleneamino-propylideneamino)-2,4,6-triiodobenzoyl]-N-methyl-β-amino-α-methylpropionic acid, melting point:- 128° to 140° C.

3-(3'-N-Allyl-carbamyl-2',4',6'-triiodoanilino)-3-methylamino-propylidene-(3)-carboxylic acid, melting point:- 125° to 134° C.

3-(3'-N-Methyl-carbamyl-2',4',6'-triiodoanilino)-3-diethylamino-propylidene-(3)-carboxylic acid, melting point:- 209° to 213° C.

3-(3'-N-Ethyl-carbamyl-2',4',6'-triiodoanilino)-3-diethylamino-propylidene-(3)-carboxylic acid, melting point:- 118° to 128° C.

3-(3'-N-Allyl-carbamyl-2',4',6'-triiodoanilino)-3-diethylamino-propylidene-(3-)-carboxylic acid, melting point:- 109° to 130° C.

3-[3'-(3''-Oxapentamethylene-carbamyl)-2',4',6'-triiodo-anilino]-3-diethylamino-propylidene-(3)-carboxylic acid, melting point:- 142° to 150° C.

3[-3'-(3''-Oxapentamethylene-carbamyl)-2',4',6'-triiodo-anilino]-3-(3''''-oxtapentamethyleneamino)-propylidene-(3)-carboxylic acid, melting point:- 145° to 155° C.

3-(1'-Dimethylamino-ethylideneamino)-5-N-methylcarbamyl-2,4,6-triiodobenzoic acid hydrochloride, melting point:- 243° to 249° C. with decomposition.

N-[3-(1'-3''-Oxapentamethyleneamino-ethylideneamino)-2,4,6-triiodobenzoyl]-β-aminobutyric acid, melting point:- 140° to 150° C.

N-[3-(1'-3''-Oxapentamethyleneamino-2'-methyl-propylidene-amino)-2,4,6-triiodobenzoyl]-β-amino-α-methylpropionic acid, melting point:- 110° to 125° C.

N-[3-(1'-3''-Oxapentamethyleneamino-2'-methylpropylideneamino)-2,4,6-triiodobenzoyl]-N-δ-methoxypropylpropionic acid, melting point:- 85° to 100° C.

N-[3-(1'-Methylamino-ethylideneamino)-2,4,6-triiodobenzoyl]-β-amino-α-methylpropionic acid, melting point:- 165° to 183° C.

The acids may be converted into the corresponding salts by treatment with alkali metal hydroxides or solutions of orgaic amines. The salts may be isolated as an amorphous product by evaporation, or may be isolated by crystallisation from suitable solvents such as water or an alcohol, or by precipitation from their solutions.

For example, the sodium salt of N-(3-dimethylaminomethyleneamino-2,4,6-triiodobenzoyl)-aminoacetic acid may be precipitated from aqueous solution by means of acetone; melting point:- 190° to 207° C.

EXAMPLE 16

2.5 kg. of N-[3-(1'-3''-oxapentamethyleneaminoethylidecamino)-2',4',6'-triiodobenzoyl]-β-amino-α-methylpropionic acid are worked into a paste with 1 l. of starch gluten containing 50 g. of corn starch, and the paste is granulated in a machine and dried in vacuo. The resulting granules are mixed with 0.25 kg. of corn starch and 12 g. of magnesium stearate and are pressed to give tablets in which the active substance content is 500 mg.

EXAMPLE 17

If dragées are desired, the granules described in Example 16 are dragée-coated by the application of sugar syrup (20% of their weight) and are subsequently waxed.

EXAMPLE 18

The sodium salt of N-[3-(1'-3''-oxapentamethyleneaminoethylideneamino)-2',4',6'-triiodobenzoyl]-β-amino-α-methylpropionic acid is filled into gelatine capsules holding 500 mg. each. For filling by machine, the salt is converted into a free-flowing paste with ground nut oil. Instead of the sodium salt, the free acid, in a finely divided form, may be employed.

EXAMPLE 19

To prepare effervescent granules, 300 g. of the sodium salt of N-[3-(1'-3''-oxapentamethyleneaminoethylideneamino)-2',4',6'-triiodobenzoyl]-β-amino-. propionic acid, 337.5 g. of tartaric acid, 1.22 g. of polyoxystearate (sic), 1.22 g. of sodium laurylsulphonate, 300 g. of caster sugar and 265 g. of sodium carbonate are well mixed, moistened with alcohol and converted into granules. The amount indicated suffices for 100 portions.

EXAMPLE 20

300 g. of N-[3-(1'-3''-oxapentamethyleneaminoethylideneamino)-2',4',6'-triiodobenzoyl]-β-amino-α-methylpropionic acid, 275 g. of sugar, 2.5 g. of Texapon, 7.5 g. of citric acid, 10 g. of Polyfibron and 5 ml. of orange essence are thoroughly homogenised and packaged in portions of 6 g. Before administration, the mixture is shaken up in water, and it is then taken orally.

EXAMPLE 21

The salt described in Example 18, in the form of a concentrated solution in polyethylene glycol 300, is filled into gelatine capsules. The capsules contain 500 mg. of active compound.

EXAMPLE 22

697.0 g. of N-[3-(1'-3''-oxapentamethyleneaminoethylideneamino)-2,4,6-triiodobenzoyl]-β-aminopropionic acid are taken up in an aqueous solution of 193.2 g. of N-methylglucamine and made up to 2,323 ml. with doubly distilled water. After fine filtration, the solution is filled into ampoules holding 10 or 20 ml. and sterilised. It may be used for injection purposes and contains 3 g. of free acid per 100 ml. of solution.

What we claim is:

1. A compound selected from the group consisting of compounds of the formula

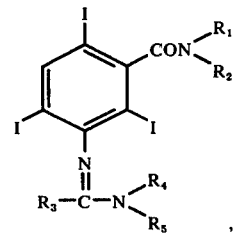

lower alkyl esters thereof and pharmaceutically acceptable salts thereof, wherein $R_1$ is selected from the group consisting of hydrogen, alkyl of up to 4 carbon atoms, alkenyl of up to 4 carbon atoms and alkoxyalkyl of up to 6 carbon atoms, $R_2$ is selected from the group consisting of lower alkyl and lower alkenyl, $R_3$ is alkylenecarboxylic acid group of up to 4 carbon atoms, $R_4$ is selected from the group consisting of hydrogen and lower alkyl, and $R_5$ is selected from the group consisting of alkyl of up to 4 carbon atoms, alkenyl of up to 4 carbon atoms and alkoxyalkyl of up to 6 carbon atoms.

2. A compound according to claim 1 selected from the group consisting of compounds of the formula

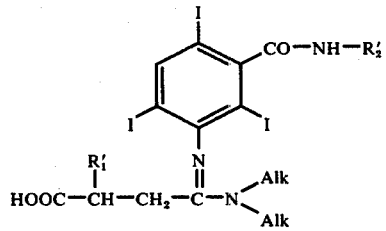

lower alkyl esters thereof and pharmaceutically acceptable salts thereof, wherein $R_2'$ is selected from the group consisting of methyl, ethyl and allyl, $R_1'$ is selected from the group consisting of hydrogen and methyl, and Alk is selected from the group consisting of methyl and ethyl.

3. A compound according to claim 2 namely 3-(3'-N-Methylcarbamyl-2',4',6'-triiodoanilino)-3-diethylamino-propylidene-(3)-carboxylic acid, its lower alkyl ester or pharmaceutically acceptable salt.

4. A compound according to claim 2 namely 3-(3'-N-Allylcarbamyl-2',4',6'-triiodoanilino)-3-diethylamino-propylidene-(3)-carboxylic acid, its lower alkyl ester or pharmaceutically acceptable salt.

5. A compound according to claim 1 namely 3-(3'-N-ethylcarbamyl-2',4',6'-triiodoanilino)-3-diethylamino-propylidene-(3)-carboxylic acid, its lower alkyl ester or pharmaceutically acceptable salt.

* * * * *